United States Patent
Lombardi et al.

[11] Patent Number: 5,951,463
[45] Date of Patent: Sep. 14, 1999

[54] HAND-HELD ENDOSCOPIC VIEWING SYSTEM

[75] Inventors: Steve Lombardi, New Brighton; Craig Riedl, Long Lake; Mark F. Brown, Fridley; Thomas C. Barthel, Becker, all of Minn.

[73] Assignee: Clarus Medical Systems, Inc., Minneapolis, Minn.

[21] Appl. No.: 09/040,759

[22] Filed: Mar. 18, 1998

[51] Int. Cl.$^6$ .................................................. A61B 1/002
[52] U.S. Cl. ................................ 600/162; 60/163; 60/172
[58] Field of Search .................................. 600/112, 125, 600/133, 131, 136, 160, 162, 167, 172, 174, 175, 182, 163

[56] References Cited

U.S. PATENT DOCUMENTS

| | | |
|---|---|---|
| 728,589 | 5/1903 | Levi . |
| 2,290,665 | 7/1942 | Arnesen . |
| 3,224,320 | 12/1965 | Knudsen . |
| 3,297,022 | 1/1967 | Wallace ..................................... 600/172 |
| 3,434,775 | 3/1969 | Gosselin ................................... 600/175 |
| 4,440,157 | 4/1984 | Shishido ................................... 600/162 |
| 4,561,446 | 12/1985 | Hetz . |
| 4,580,198 | 4/1986 | Zinnanti, Jr. . |
| 4,616,630 | 10/1986 | Arakawa . |
| 4,624,243 | 11/1986 | Lowery .................................... 600/163 |
| 4,736,733 | 4/1988 | Adair ....................................... 600/162 |
| 4,742,818 | 5/1988 | Hughes ..................................... 600/163 |
| 4,762,120 | 8/1988 | Hussein . |
| 4,782,819 | 11/1988 | Adair . |
| 4,784,118 | 11/1988 | Fantone ................................... 600/160 |
| 4,958,932 | 9/1990 | Kegelman ................................. 600/172 |
| 5,088,819 | 2/1992 | Storz . |
| 5,125,394 | 6/1992 | Chatenever ............................... 600/162 |
| 5,152,278 | 10/1992 | Clayman ................................... 600/131 |
| 5,183,031 | 2/1993 | Rossoff . |
| 5,184,602 | 2/1993 | Analpiotis ................................. 600/172 |
| 5,215,077 | 6/1993 | Oku .......................................... 600/175 |
| 5,359,453 | 10/1994 | Ning ......................................... 600/182 |
| 5,368,014 | 11/1994 | Anapliotis et al. ....................... 600/162 |
| 5,377,668 | 1/1995 | Ehmsen .................................... 600/162 |
| 5,582,575 | 12/1996 | Heckele .................................... 600/175 |
| 5,588,949 | 12/1996 | Taylor et al. . |
| 5,588,950 | 12/1996 | Sano et al. . |
| 5,607,386 | 3/1997 | Flan . |
| 5,630,788 | 5/1997 | Forkner .................................... 600/162 |
| 5,636,625 | 6/1997 | Miyagi et al. . |
| 5,645,519 | 7/1997 | Lee et al. . |

*Primary Examiner*—John P. Leubecker
*Attorney, Agent, or Firm*—Olson & Hierl, Ltd.

[57] ABSTRACT

A hand held endoscopic viewing system including a viewing assembly, an eyepiece assembly, and a handle is disclosed. The components are releasably mounted for ease of use and cleaning. The viewing assembly incorporates a fiber optic image bundle for carrying an image to the eyepiece assembly. The proximal end of the image bundle terminates in a coupling assembly that couples the eyepiece assembly to the viewing assembly such that the proximal end of the image carrying bundle is held against a window on the eyepiece assembly. The eyepiece assembly includes focusing optics that define a focal plane at the distal plane of the window for focusing and magnifying the image that is carried to the proximal end of the image bundle. The handle includes a light source and a power source and supports the eyepiece assembly and the viewing assembly at two points.

26 Claims, 6 Drawing Sheets

HAND-HELD ENDOSCOPIC VIEWING SYSTEM

FIELD OF THE INVENTION

The present invention relates to an endoscope having releasably mounted components for ease of use and cleaning.

BACKGROUND OF THE INVENTION

Many types of endoscopes currently use a fiber optic viewing bundle that cooperates with a focusing eyepiece assembly to permit viewing within a body cavity. The fiber optic bundle and any associated connectors can be generally referred to as a viewing assembly. The fiber optic bundle usually includes an image bundle that is a coherent bundle of image carrying fibers and at least one illumination carrying bundle or fiber. The image bundle typically cooperates with the focusing eyepiece. The end of the image bundle usually terminates in a connector that cooperates with the eyepiece.

The illumination fibers are typically adapted to cooperate with a light source. The ends of the image bundle and the illumination fibers are usually coterminal at the distal end of the endoscope. The illumination fibers carry light from a light source to the distal end of the endoscope in order to illuminate the area in front of the endoscope. An image of the illuminated area is then carried back through the endoscope to the eyepiece via the image bundle.

Many versions of endoscopic devices also include a handle that holds the eyepiece and the fiber optic bundle and associated connectors. Some hand held endoscopic viewing devices include a power source and a light source associated with the handle. Also, the handle can be configured to connect to the fiber optic bundle and to the eyepiece to hold the entire system in operable relationship.

The eyepiece assembly of a typical endoscope can be used with the naked eye of the operator or, alternatively, can be configured to connect to a camera or an electronic monitor to provide still photographs or video images. Focusing eyepieces generally include precision optics and moving parts such as rotating rings or sliding tubes. The spacing between the end of the image bundle or connector and the eyepiece must be exact for proper focus. These instruments are generally made with precision components and are therefore relatively expensive and can be very delicate. Also, the step of focusing the eyepiece takes time and requires additional manipulation of the endoscope. This can be a disadvantage in emergency situations. A fixed-focus eyepiece that is quickly and easily cleaned, assembled, and used provides a great advantage.

Another advantage of a viewing system that can be disassembled into various parts such as the viewing assembly, the eyepiece assembly, and the handle is that each separate part can be replaced if necessary. Typically, fiber optic components that are used in the viewing assemblies are somewhat delicate and have a limited life span. For example, the fiber optic bundles are often bent or twisted during use. The repeated stresses of bending and twisting can cause the optic fibers to break. However, as components are removed and replaced it is often necessary to refocus the endoscope before it can be used.

It is desirable to provide a viewing assembly that includes a minimal number of parts that can be relatively inexpensive to replace. Also, the replaceable components should be easily manufactured in order to keep the cost of the replaceable parts as low as possible. Given the precise nature of most endoscopes, it would be an advantage to provide an endoscopic viewing system that is more easily manufactured.

Many common endoscopes are also relatively complicated in structure. Since endoscopes are typically used for sterile surgical procedures, the complicated structure makes sterilization of the instrument difficult. Also, some sterilization procedures are harmful to eyepiece optics and other more delicate components. It would therefore be an advantage to provide an endoscopic viewing assembly that is relatively simple to manufacture and use and that is easily sterilized. A simplified, fixed focus eyepiece assembly that has no moving parts and that is sealed from the outside world would also be an advantage.

Accordingly, what is needed is an endoscopic viewing system that allows for relatively easy replacement of any particular component that may become dirty, contaminated, or damaged during use. The portion of the device that comes in contact with the patient should be separately sterilizable to avoid damage to eyepiece optics. The present invention meets these desires.

SUMMARY OF THE INVENTION

An endoscopic viewing system embodying the present invention comprises a viewing assembly removably mounted on an eyepiece assembly, such as by a coupling assembly. The eyepiece assembly includes a body carrying focusing optics, and the viewing assembly includes an image bundle.

The eyepiece assembly preferably includes a body carrying focusing optics and having a distal portion and a proximal portion. The eyepiece assembly focuses and magnifies the image carried by the fiber optic image bundle. The body of the eyepiece assembly is preferably cylindrical.

The distal portion of the body includes an optical aperture such as a window that defines a distal plane, and the focusing optics have a focal plane fixed substantially at the distal plane. The image bundle has a proximal end that is substantially adjacent to the focal plane of the focusing optics when the eyepiece assembly and the viewing assembly are coupled. The proximal end of the image bundle preferably is planar and flatly contacts the window of the eyepiece assembly when the eyepiece assembly and the viewing assembly are coupled.

An image carried from the body cavity through the image bundle is focused and magnified by the eyepiece assembly. The planar proximal end of the image bundle places the image on the focal plane when the proximal end contacts the window of the eyepiece assembly. Focusing adjustment is not required because the proximal end of the image bundle is always at the focal plane when the viewing assembly and the eyepiece assembly are coupled.

A handle can also be provided in the preferred embodiment for holding the eyepiece assembly and the viewing assembly. The handle includes a clasp that releasably engages the body of the eyepiece assembly and a first connector that releasably engages a second connector on the viewing assembly.

The fixed-focus eyepiece assembly provides the advantage of quick and easy assembly and use with a viewing assembly. Also, the window of the eyepiece assembly provides a seal to protect the interior optical and mechanical components from liquids and foreign material. The liquid-tight seal allows the user to effectively clean the eyepiece assembly and assures compatibility with immersion methods of sterilization.

Moreover, since the eyepiece assembly and the viewing assembly are easily separable from each other, they can be separately replaced during use if one becomes contaminated without replacing or re-sterilizing the other. Since the eyepiece assembly and the handle do not come in patient contact, they can be either disinfected or sterilized, depending on the protocol of the facility using the viewing system.

Numerous other advantages of the present invention will become readily apparent to those skilled in the art from the following detailed description of the preferred embodiment of the invention, the drawings, and the appended claims.

DETAILED DESCRIPTION OF THE PREFERRED EMBODIMENTS

While this invention can be embodied in many different forms, there is shown in the drawings and described in detail preferred embodiments of the invention. The present disclosure of an exemplification of the principals of the invention and is not intended to limit the invention to the embodiments illustrated.

Figures 1, 2:
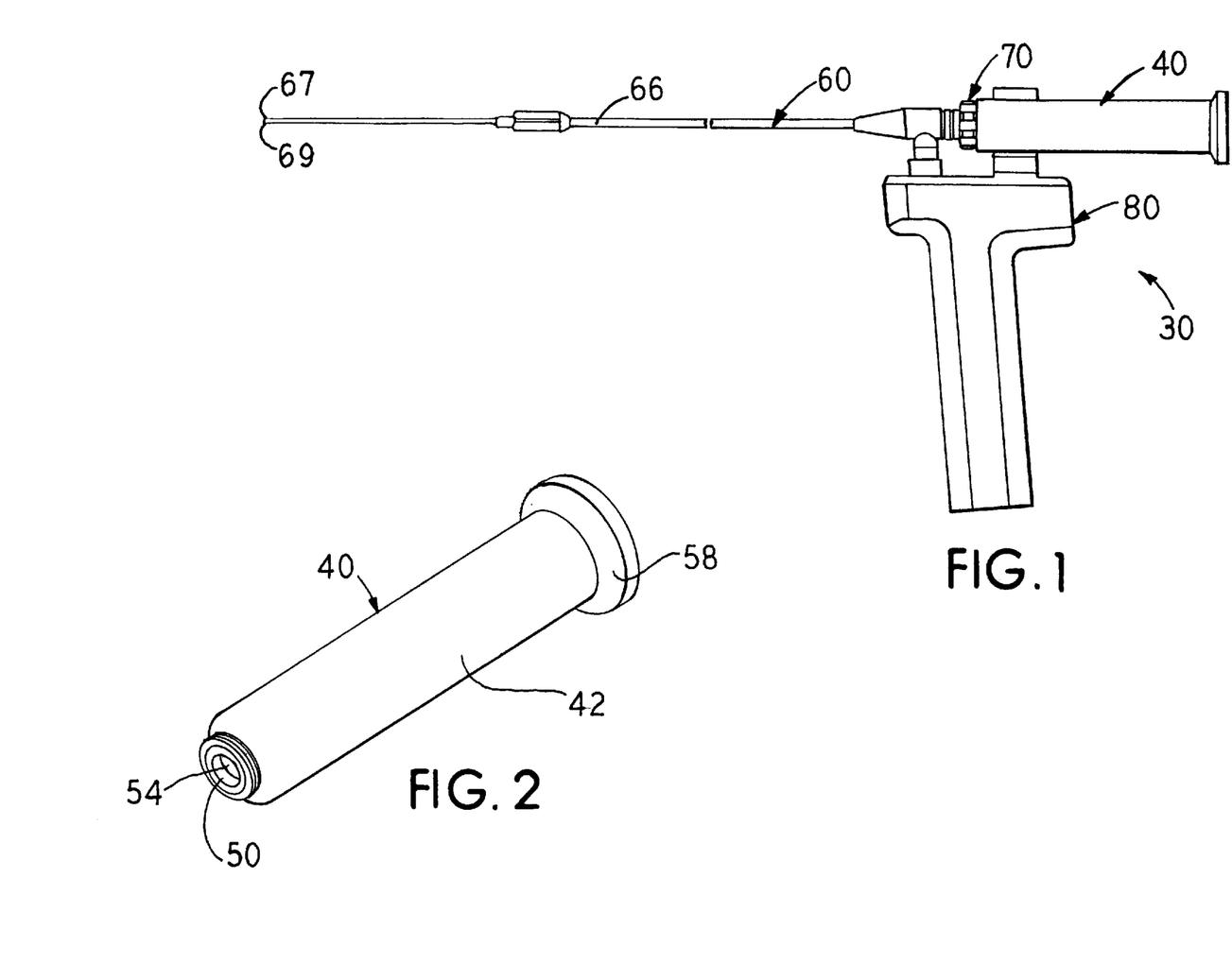
FIG. 1 is a side elevational view of an endoscopic viewing system of the present invention showing a viewing assembly coupled to an eyepiece assembly mounted on a handle.
FIG. 2 is a perspective view of the eyepiece assembly.

Referring to FIG. 1 of the drawings, one embodiment of the present invention, an endoscopic viewing system 30 is shown. The viewing system 30 includes an eyepiece assembly 40, a viewing assembly 60, and a handle 80.

Figure 3:
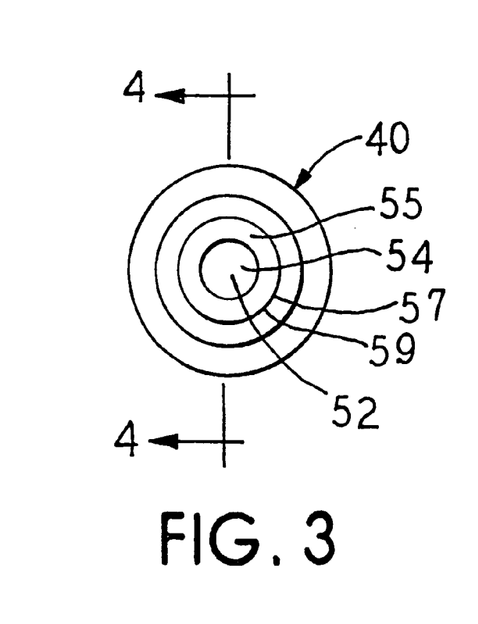
FIG. 3 is an end view of the eyepiece assembly.
Figure 4:
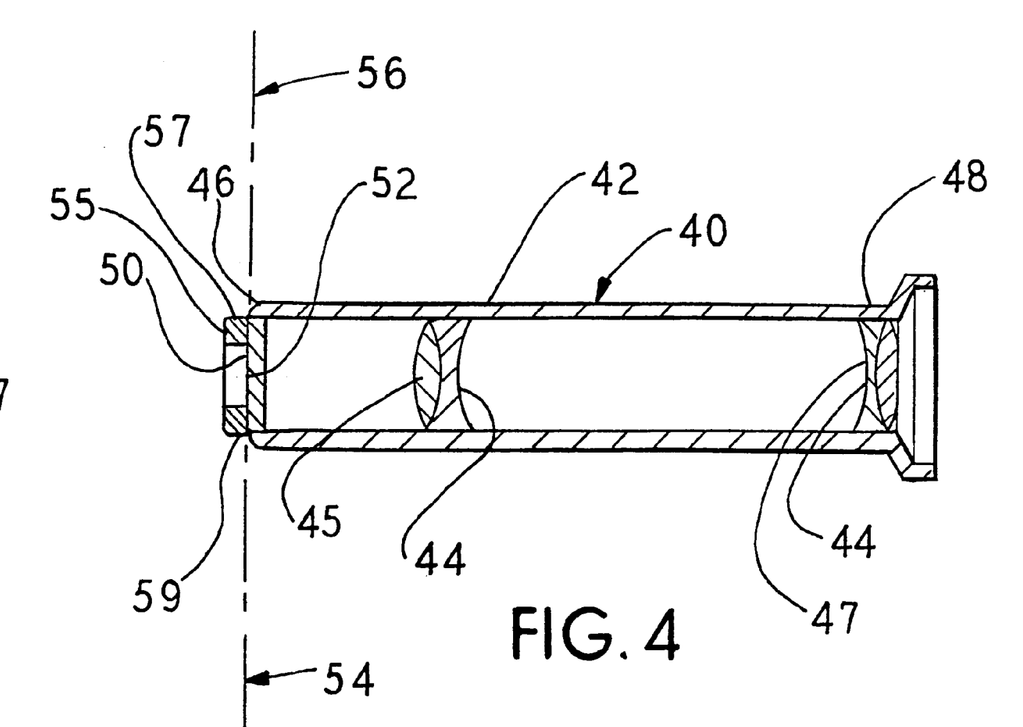
FIG. 4 is a cross-sectional view of the eyepiece assembly taken along line 4—4 of FIG. 3.

Referring to FIGS. 2–4, the eyepiece assembly 40 includes a body 42 carrying focusing optics 44 and having a distal portion 46 and a proximal portion 48. The body 42 is preferably cylindrical. The focusing optics 44 include two groupings of lenses commonly referred to as doublets. The doublet closest to the distal portion 46 is the objective 45, and the doublet closest to the proximal portion 48 is the eyepiece doublet 47.

The distal portion 46 of the eyepiece assembly 40 includes an optical aperture 50 that allows light to pass into the body 42 and through the focusing optics 44. The optical aperture 50 can be defined as a physical opening, but preferably is a window 52 that seals the inside of the eyepiece from the outside world. The outside surface of the window 52 defines a distal plane 54 substantially perpendicular to the axis of the body 40. Alternatively, the optical aperture 50 can be defined by a ring or similar structure that has an exterior surface that defines a contact surface for the distal plane. The contact surface is thus disposed about the optical aperture 50. Such a ring can be combined with the window.

The focusing optics 44 have a focal plane 56 fixed substantially at the distal plane 54 and preferably at the same plane as shown in FIG. 4. The focal plane 56 is the plane perpendicular to the principal axis of the focusing optics 44 where the best image is formed.

The window 52 is preferably made of sapphire and the focusing optics 44 are made of optical quality glass. The focusing optic can be made as is well known in the art.

A mating ring 55 surrounding the window 52 at the distal potion 46 is provided in the preferred embodiment for coupling the eyepiece assembly 40 to the viewing assembly 60 as described below. The proximal end 48 of the body 42 preferably includes an eyecup 58. Alternatively, the eyecup 58 can be removed or adapted for attachment of a camera or electronic monitor to the eyepiece assembly.

A preferred embodiment of the viewing assembly 60 is shown in FIGS. 5–8. The viewing assembly 60 includes a fiber optic image bundle 62 having a proximal region 63 terminating in a planar proximal end 64. The planar proximal end 64 is substantially adjacent and preferably at the focal plane 56 when the eyepiece assembly 40 is coupled with the viewing assembly 60, as described in further detail below. The planar proximal end 64 can be in contact with the window 52 or the contact surface discussed above. It is preferred that the planar proximal end be in flat contact with the window, i.e. its plane is the same as the focal plane 56.

Figure 5:
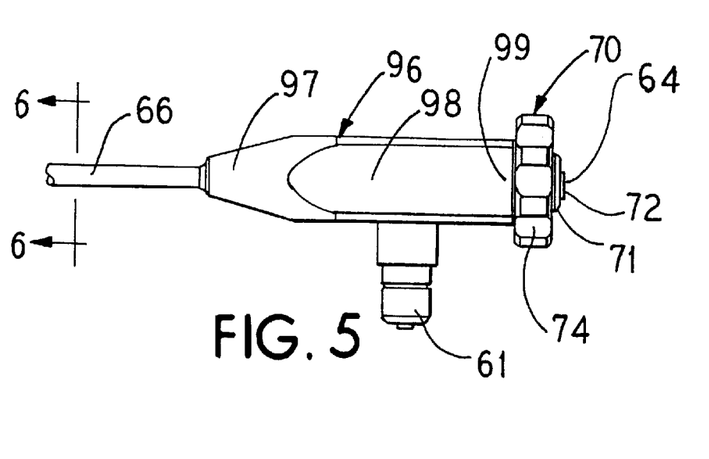
FIG. 5 is a partial side elevational view of the viewing assembly of FIG. 1 showing a coupling assembly and a second connector.
Figure 8:
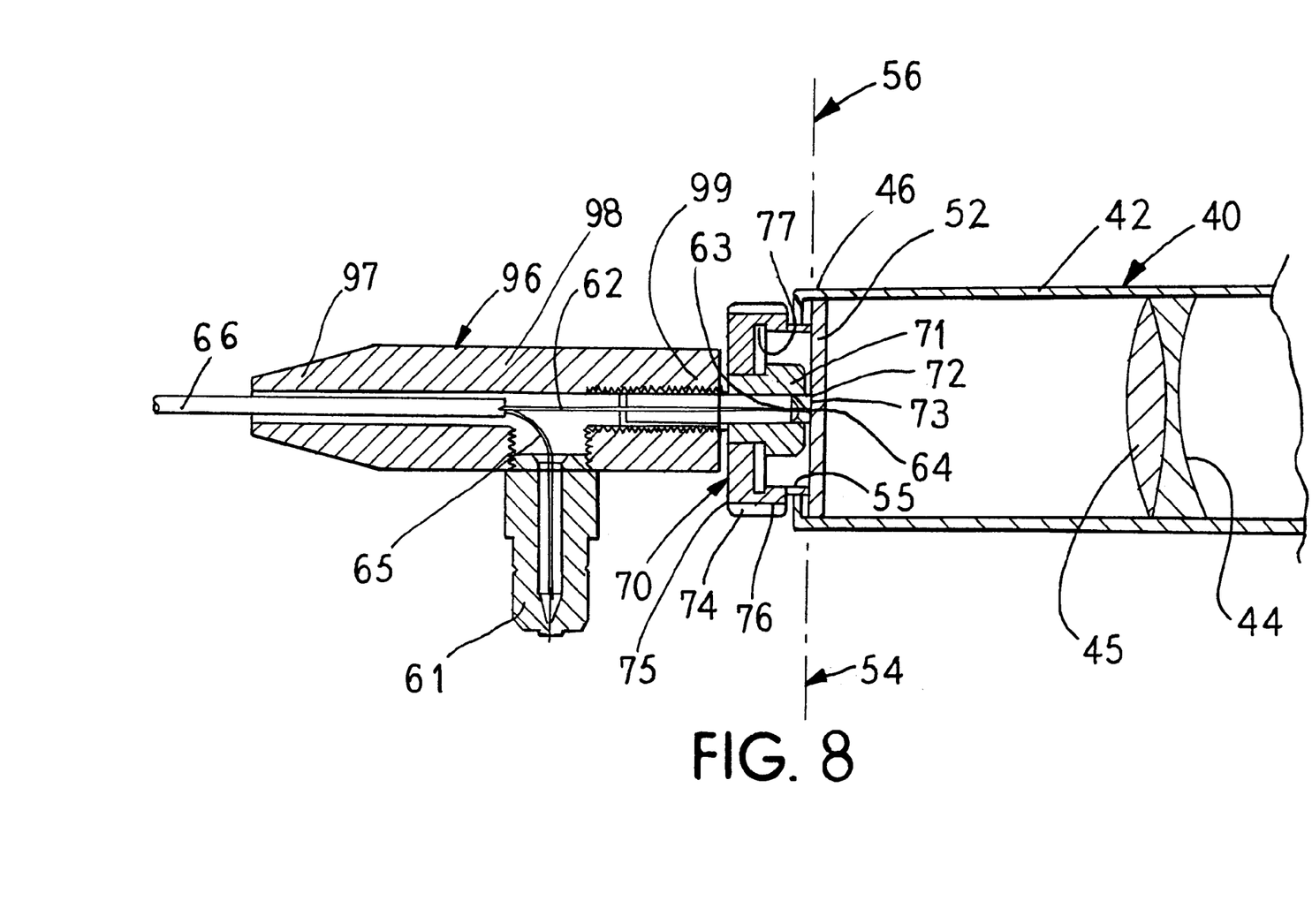
FIG. 8 is a partial cross-sectional view of the viewing assembly taken along line 8—8 of FIG. 7 showing the viewing assembly coupled to the eyepiece assembly.

Referring to FIGS. 5 and 8, a preferred embodiment of the viewing assembly 60 includes a housing 96 having a forward portion 97, a middle portion 98, and a rearward portion 99. The image bundle 62 preferably enters the housing 96 at the forward portion 97. The proximal region 63 including the proximal end 64 of the image bundle 62 extends into the rearward portion 99.

A coupling assembly 70 is provided at the rearward portion 99 in the preferred embodiment. The coupling assembly 70 is described in detail below.

In use, the image bundle 62 carries an image from its distal end 67 to the planar proximal end 64. The image can then be viewed through the eyepiece assembly 40 because the focusing optics 44 magnify and focus the image at the focal plane 56. Preferably, the image bundle 62 is a 30,000 pixel coherent bundle of fibers. Image bundles are commonly available in the range of about 3,000 pixels to about 50,000 pixels with corresponding diameters of about 250 $\mu$m to about 1100 $\mu$m. The fibers are commonly made of glass. Examples of image bundles that are suitable for use in the preferred embodiment are available from Sumitoma or Mitsubishi. The dimensions and materials of the image bundle 62 can be varied for any particular application as desired.

Figure 6:
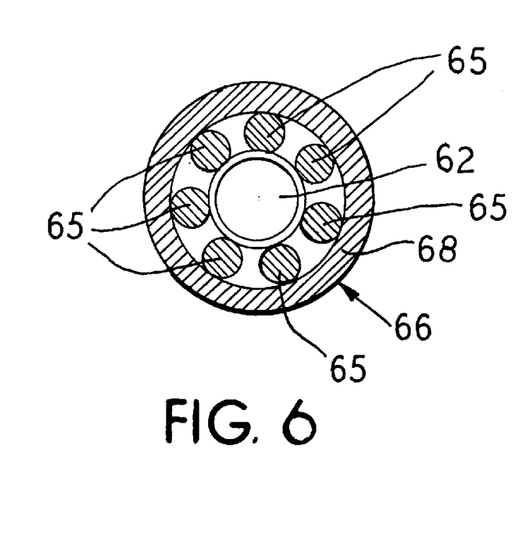
FIG. 6 is a cross-sectional view of the viewing assembly taken along line 6—6 of FIG. 5 and showing an image bundle and illumination fibers.

The image bundle 62 is preferably part of a fiber optic bundle 66 that also includes illumination fibers 65 as shown in FIG. 6. A preferred embodiment of the fiber optic bundle 66 includes seven illumination fibers 64 (also commonly referred to as light fibers) surrounding the image bundle 62. The illumination fibers 64 preferably are about 500 $\mu$m in diameter.

The fiber optic bundle 66 further includes a jacket 68 surrounding the image bundle 62 and the illumination fibers 65. The jacket 68 protects the bundle and fibers.

A preferred embodiment of the viewing system 30 also includes the coupling assembly 70 for coupling the viewing assembly 60 to the eyepiece assembly 40. Referring again to FIGS. 7 and 8, the coupling assembly 70 preferably includes a collar 71 on the viewing assembly 60 which engages a retaining ring 74 on the viewing assembly 60. The collar 71 is preferably fixed to and surrounds the proximal end 64 of the image bundle 62. The retaining ring 74 rotatably surrounds the collar 72.

Figure 7:
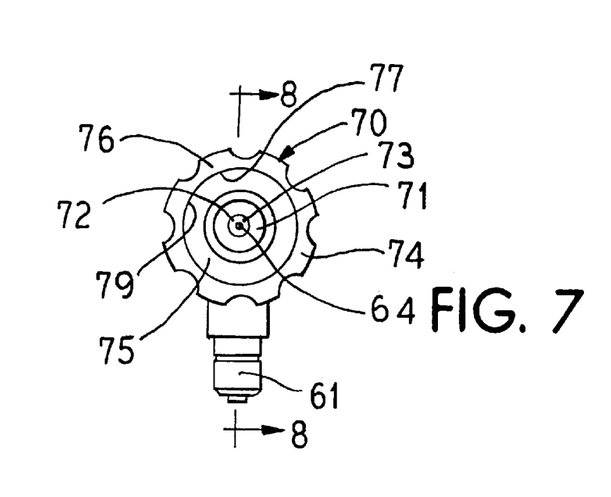
FIG. 7 is an end view of the viewing assembly showing the coupling assembly and the second connector.

The collar 71 includes a central raised portion 72 that has a proximal surface 73 that is substantially coplanar with the proximal end 64 of the image bundle 62. This coplanar configuration allows the proximal end 64 of the image bundle 62 to be fixed substantially at the focal plane 56 when the viewing assembly 60 is coupled to the eyepiece assembly 40. Preferably, the proximal surface 73 of the central raised portion 72 is coplanar with the proximal end 64, and the proximal end 64 and the proximal surface 73 together contact the window 52. The proximal surface 73 can alternatively contact a contact surface as discussed above. The image carried to the proximal end 64 can then be viewed without necessitating focusing adjustment.

The proximal surface 73 is preferably polished to an optically functional finish. The polishing is preferably performed while the proximal region 63 of the image bundle 62 is mounted within the collar 71 with the proximal end 64 extending beyond the proximal surface 73. This procedure allows the proximal end 64 of the image bundle 62 and the proximal surface 73 of the central raised portion 72 to be substantially coplanar after being polished together. An advantage of performing the polishing after assembling the image bundle 62 to the collar 71 is ease of manufacture. The proximal surface 73 can be polished without fear of removing to much or too little material, because the proximal surface 73 preferably physically contacts the window 52 or the contact surface and therefore does not need to be precisely ground in relation to the focal plane 56.

Referring to FIGS. 7 and 8, the retaining ring 74 preferably includes a cylindrical portion 76 having a retaining mechanism 77. The retaining mechanism 77 of the preferred embodiment is a threaded inner surface 79 that cooperates with a corresponding mating mechanism 57 such as a threaded outer surface 59 on the mating ring 55 of the eyepiece assembly. Alternatively, the retaining and mating mechanisms 77 and 57 can be in the form of a bayonet mounting mechanism or any suitable connecting mechanism.

The retaining ring 74 also includes a disk portion 75 that is unitary or integral with the cylindrical portion 76. As the retaining ring 74 is rotated to engage the mating ring 55, the cylindrical portion 76 and disk portion 75 are moved longitudinally toward the proximal surface 73 of the collar 71. The collar 71 is urged by the disk portion 75 toward the window 52 or contact surface until the proximal end 64 of the image bundle 62 contacts the window 52 or contact surface. At this point, the eyepiece and viewing assemblies are coupled, and the image carried by the image bundle 62 is substantially adjacent to the focal plane 56 and is viewable through the eyepiece assembly 40.

Figure 9:
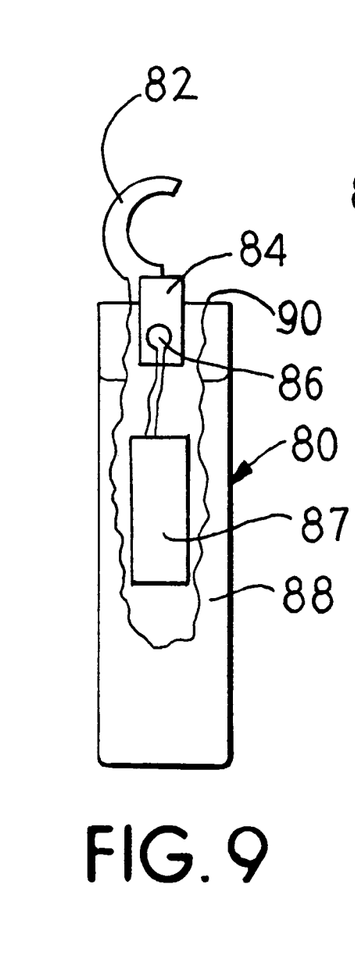
FIG. 9 is a partial broken front view of the handle of the viewing system.
Figure 10:
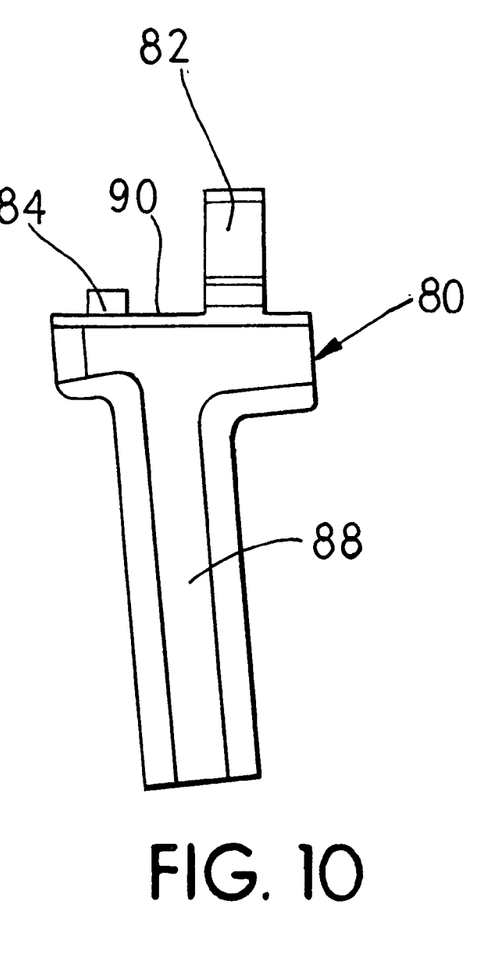
FIG. 10 is a side elevational view of the handle.

After the eyepiece and viewing assemblies are coupled, they can be mounted to a handle 80, as shown in FIG. 1. FIGS. 9 and 10 show a preferred embodiment of the handle 80 of the viewing system 30.

The handle 80 includes a clasp 82 and a first connector 84. The handle 80 holds the eyepiece and viewing assemblies 40 and 60 by releasably engaging the body 42 of the eyepiece assembly 40 with the clasp 82. The clasp 82 is preferably a generally C-shaped body that cooperates with the cylindrical body 42 of the eyepiece assembly 40. The combined eyepiece and viewing assemblies are mounted on the handle 80 by inserting a second connector 61 of the viewing assembly 60 in the first connector 84 and rotating the combination about the axis of the connectors until the body 42 is releasably engaged by the clasp 82.

As shown in FIGS. 9 and 10, the handle 80 includes a gripping portion 88 and a top side 90 spaced from the gripping portion 88. The first connector 84 and the clasp 82 are located on the top side 90 in spaced relationship to each other. The first connector 84 releasably engages the second connector 61 on the viewing assembly 60.

The second connector 61 preferably is disposed on the middle portion 98 of the housing 96 of the viewing assembly 60. As shown in FIGS. 5 and 8, the second connector 61 is at a generally perpendicular orientation on the housing 96 with respect to the axis of the coupling assembly 70. The first and second connectors 84 and 61 preferably releasably engage each other in a snap fit manner, but can be embodied in any configuration known in the art.

The handle 80 includes an illumination source 86 operably associated with the first connector 84. The illumination fibers 65 of the viewing assembly are operably associated with the second connector 61. When the first and second connectors 84 and 61 are engaged, the illumination source 86 can provide light to the distal end 69 of the fiber optic bundle 66 to illuminate the body cavity or area which is to be viewed.

A power source 87 can be provided within the handle to supply power to the illumination source 86. Preferably, the illumination source 86 is an incandescent lamp powered by four 1.5 volt AA lithium batteries. Alternatively, the power source can be an external source of AC or DC current.

When the viewing system is assembled, the handle 80 supports the eyepiece assembly 40 and the viewing assembly 60 at two spaced-apart points. This configuration provides a stable viewing system that can be easily controlled by manipulation of the handle 80.

Figure 11:
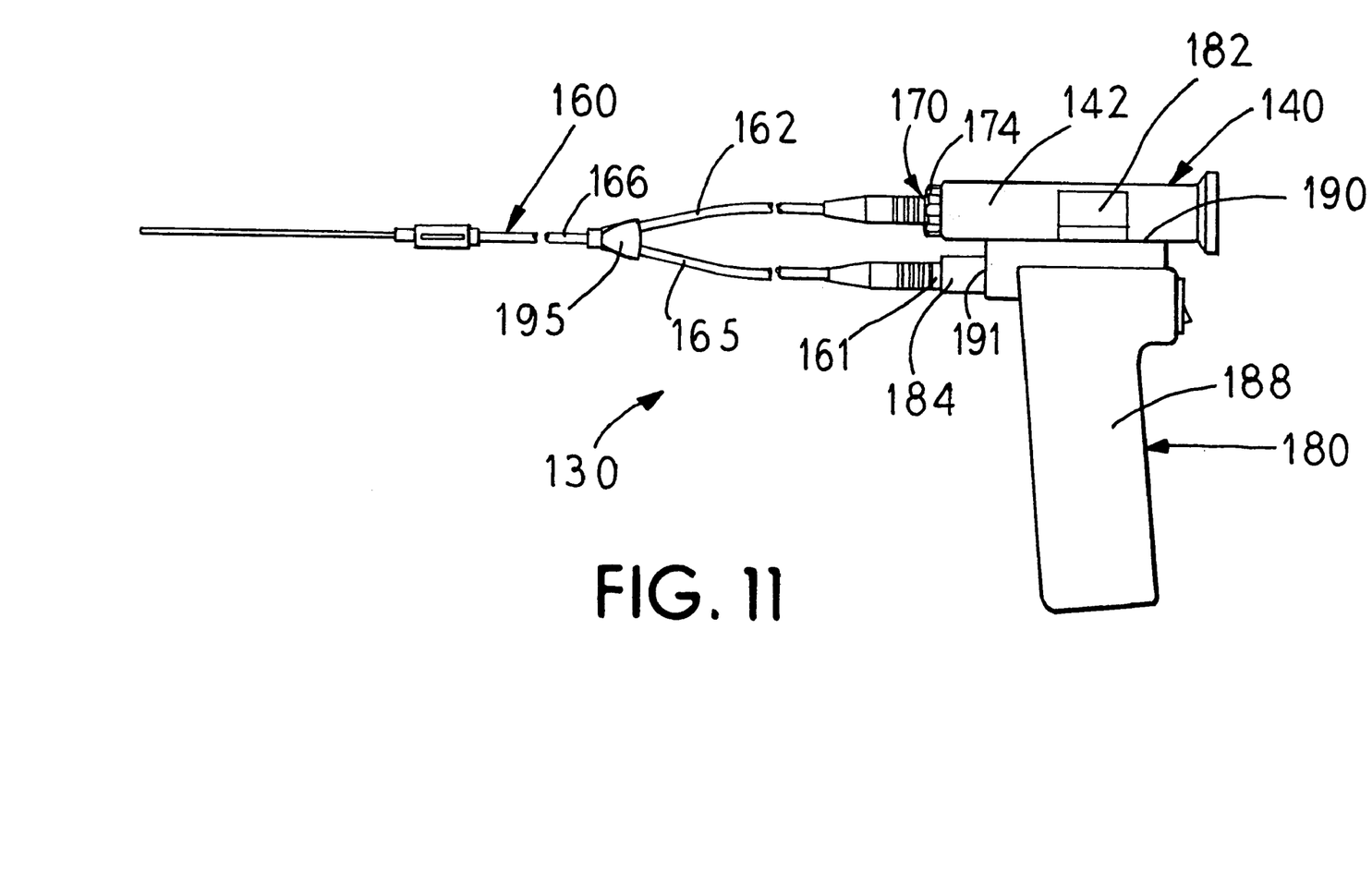
FIG. 11 is a side elevational view of an alternate embodiment of a viewing system.

An alternate embodiment of a viewing system 130 of the present invention is shown in FIG. 11. Viewing system 130 includes alternate embodiments of a viewing assembly 160 and a handle 180, but can include the previously described eyepiece assembly 40 of FIGS. 2–4.

Handle 180 includes a clasp 182, a first connector 184, a gripping portion 188, a top side 190, and a front side 191; the top and front sides 190 and 191 being spaced from the gripping portion 188. The clasp 182 is located on the top side 190, but in this alternate embodiment, the eyepiece assembly 140 is releasably engaged with the clasp 182 by inserting the eyepiece assembly 140 downwardly into the clasp 182. The clasp 182 releasably engages the eyepiece assembly 140 by frictionally gripping the body 142 of the eyepiece assembly 140.

The first connector 184 of the alternate embodiment is located on the front side 191 of the handle 180. The alternate location of the first connector 184 necessitates an alternate embodiment of the viewing assembly 160 so that the components can all be operably associated as previously described with respect to the preferred embodiment.

The viewing assembly 160 shown in FIG. 11 includes a second connector 161, a coupling assembly 170, and a junction body 195. A fiber optic bundle 166 extends distally from the junction body 195 and includes an image bundle 162 and illumination fibers 165, as shown in FIG. 11. Proximal of the junction body 195, the image bundle 162 and the illumination fibers 165 extend separately from each other. Image bundle 162 includes a planar proximal end 164.

The illumination fibers 165 terminate in a second connector 161, and the image bundle 162 terminates in a coupling assembly 170. Second connector 161 is releasably engaged with first connector 184 on the handle 180, and coupling assembly 170 is releasably engaged with an eyepiece assembly 140.

Because the viewing assembly 160 includes the second connector 161 and the coupling assembly on separate extensions from the junction body 195, the viewing assembly 160 can be used with any number of handles that have the first connector 184 at any location such as, for example, on any side or at the bottom of the handle. Also, viewing assembly 160 can be used with an illumination source that is not included in the handle.

Although the invention has been described with reference to certain preferred embodiments, numerous modifications and various can be made by those skilled in the art without departing from the novel spirit and scope of this invention.

What is claimed is:

1. An endoscopic viewing system comprising:
   a) an eyepiece assembly including a body carrying focusing optics and having a distal portion and a proximal portion, the distal portion including a window defining a distal plane, the focusing optics having a focal plane fixed substantially at the distal plane;
   b) a viewing assembly including an image bundle having a proximal end; and
   c) a coupling assembly for coupling the eyepiece assembly to the viewing assembly, the proximal end of the image bundle being substantially adjacent to the focal plane when the eyepiece assembly and the viewing assembly are coupled.

2. The viewing system of claim 1 wherein the proximal end of the image bundle is planar and contacts the window when the eyepiece assembly and the viewing assembly are coupled.

3. The viewing system of claim 1 wherein the viewing assembly includes a housing having a rearward portion, the proximal end of the image bundle extends into the rearward portion, the coupling assembly is provided at the rearward portion and includes a collar surrounding the proximal end of the image bundle and having a proximal surface substantially coplanar with the proximal end of the image bundle, and a retaining ring rotatably surrounding the collar.

4. An endoscopic viewing system comprising:
   a) an eyepiece assembly including a body carrying focusing optics and having a distal portion and a proximal portion, the distal portion including a window defining a distal plane, the focusing optics having a focal plane fixed substantially at the distal plane;
   b) a viewing assembly including an image bundle having a proximal end;
   c) a coupling assembly for coupling the eyepiece assembly to the viewing assembly, the proximal end of the image bundle being substantially adjacent to the focal plane when the eyepiece assembly and the viewing assembly are coupled; and
   d) a handle for holding the eyepiece assembly and the viewing assembly, the handle including a clasp releasably engaging the body of the eyepiece assembly and a first connector releasably engaging a second connector on the viewing assembly.

5. The viewing system of claim 4 wherein the handle includes a gripping portion and a top side spaced from the gripping portion, the first connector and the clasp being located on the top side in spaced relationship to each other.

6. The viewing system of claim 4 wherein the viewing assembly includes an illumination fiber operably associated with the second connector and the handle includes an illumination source operably associated with the first connector.

7. The viewing system of claim 6 wherein the clasp includes a generally C-shaped body adapted to engagably hold the eyepiece assembly body when the first and second connectors are connected and when the eyepiece assembly and the viewing assembly are coupled.

8. The viewing system of claim 4 wherein the viewing assembly includes a junction body and a fiber optic bundle extending distally from the junction body, the fiber optic bundle including the image bundle and an illumination fiber, the image bundle and the illumination fiber extending proximally from the junction body separate from each other.

9. An endoscopic viewing system comprising:
   a) an eyepiece assembly including a body carrying focusing optics and having a distal portion and a proximal portion, the distal portion including a window defining a distal plane, the focusing optics having a focal plane fixed substantially at the distal plane;
   b) a viewing assembly including an image bundle having a proximal end; and
   c) a coupling assembly on the viewing assembly for coupling the eyepiece assembly to the viewing assembly, the proximal end of the image bundle being substantially adjacent to the focal plane when the eyepiece assembly and the viewing assembly are coupled, the coupling assembly including a collar surrounding the proximal end of the image bundle and a retaining ring rotatably surrounding the collar, the collar having a proximal surface substantially coplanar with the proximal end of the image bundle, the distal portion of the eyepiece assembly including a mating ring surrounding the window for engaging with the retaining ring when the eyepiece assembly and the viewing assembly are coupled.

10. The viewing system of claim 9 wherein the retaining ring and the mating ring are threaded.

11. An endoscopic viewing system comprising:
   a) an eyepiece assembly including a body carrying focusing optics and having a distal portion and a proximal portion, the distal portion including a window defining a distal plane, the focusing optics defining a focal plane fixed substantially at the distal plane; and
   b) a viewing assembly including an image bundle having a planar proximal end, the viewing assembly being removably mounted on the eyepiece assembly with the proximal end of the image bundle being substantially adjacent to the focal plane.

12. The viewing system of claim 11 further comprising a coupling assembly for coupling the eyepiece assembly to the viewing assembly.

13. An endoscopic viewing system comprising:
   a) a handle including a clasp and a first connector;
   b) an eyepiece assembly including a body carrying focusing optics and adapted to releasably engage the clasp, the body having a distal portion, a proximal portion, and a window defining a distal plane, the focusing optics having a focal point at the distal plane;
   c) a viewing assembly including a housing having a forward portion, a middle portion, and a rearward portion, an image bundle having a proximal end extending into the rearward portion, and a second connector on the housing for connecting with the first connector of the handle; and d) a coupling assembly at the rearward portion for coupling the viewing assembly to the eyepiece assembly and for holding the proximal end of the image bundle substantially adjacent to the distal plane of the window.

14. The viewing system of claim 13 wherein the rearward portion of the viewing assembly includes a collar having a proximal surface substantially adjacent to the distal plane.

15. The viewing system of claim 13 wherein the second connector is disposed on the middle portion in a generally perpendicular orientation with respect to the axis of the coupling assembly.

16. The viewing system of claim 13 further comprising an illumination source within the handle operably associated with the first connector.

17. The viewing system of claim 16 further comprising a power source within the handle for providing power to the light source.

18. The viewing system of claim 17 further comprising at least one illumination fiber operably associated with the second connector.

19. An endoscopic viewing system comprising:
    a) an eyepiece assembly including a body carrying focusing optics and having a distal portion and a proximal portion, the distal portion defining an optical aperture and having a contact surface about the optical aperture, the focusing optics having a focal plane fixed substantially at the contact surface; and
    b) a viewing assembly including an image bundle having a proximal region terminating at a planar proximal end, the viewing assembly being removably mounted on the eyepiece assembly with the planar proximal end adjacent the contact surface.

20. The viewing system of claim 19 wherein the optical aperture is a window.

21. The viewing system of claim 20 wherein the window also defines the contact surface.

22. The viewing system of claim 19 further comprising a coupling assembly for coupling the eyepiece assembly to the viewing assembly.

23. The viewing system of claim 22 wherein the coupling assembly includes a collar fixed to and surrounding the proximal end of the image bundle and a retaining ring rotatably surrounding the collar.

24. An endoscopic viewing system comprising:
    a) an eyepiece assembly including a body carrying focusing optics and having a distal portion and a proximal portion, the distal portion defining an optical aperture and having a contact surface about the optical aperture, the focusing optics having a focal plane fixed substantially at the contact surface;
    b) a viewing assembly including an image bundle having a proximal region terminating at a planar proximal end, the viewing assembly being removably mounted on the eyepiece assembly with the planar proximal end adjacent the contact surface; and
    c) a handle for holding the eyepiece assembly and the viewing assembly, the handle including a clasp releasably engaging the body of the eyepiece assembly and a first connector releasably engaging a second connector on the viewing assembly.

25. The viewing system of claim 24 wherein the handle includes a gripping portion and a top side spaced from the gripping portion, the first connector and the clasp being located on the top side in spaced relationship to each other.

26. An endoscopic viewing system comprising:
    a) an eyepiece assembly including a body carrying focusing optics and having a distal portion and a proximal portion, the distal portion defining an optical aperture and having a mating ring surrounding the optical aperture and a contact surface about the optical aperture, the focusing optics having a focal plane fixed substantially at the contact surface;
    b) a viewing assembly including an image bundle having a proximal region terminating at a planar proximal end, the viewing assembly being removably mounted on the eyepiece assembly with the planar proximal end adjacent the contact surface; and
    c) a coupling assembly for coupling the eyepiece assembly to the viewing assembly, the coupling assembly including a collar fixed to and surrounding the proximal end of the image bundle and a retaining ring rotatable surrounding the collar for cooperating with the mating ring when the eyepiece assembly and the viewing assembly are coupled, the collar having a proximal surface substantially coplanar with the proximal end of the image bundle.

* * * * *